United States Patent
Varga et al.

(10) Patent No.: US 8,618,487 B2
(45) Date of Patent: Dec. 31, 2013

(54) METHOD AND SYSTEM FOR EVALUATING THE DISTRIBUTION OF AN ABSORBENT MATERIAL IN AN ABSORBENT ARTICLE

(71) Applicant: The Procter & Gamble Company, Cincinnati, OH (US)

(72) Inventors: Stephen Michael Varga, Loveland, OH (US); Michael Dennis Kembel, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/789,858

(22) Filed: Mar. 8, 2013

(65) Prior Publication Data

US 2013/0181133 A1    Jul. 18, 2013

Related U.S. Application Data

(63) Continuation of application No. 12/639,301, filed on Dec. 16, 2009, now Pat. No. 8,405,032.

(51) Int. Cl.
  *G01N 21/59* (2006.01)

(52) U.S. Cl.
  USPC ........................................ 250/341.1

(58) Field of Classification Search
  USPC .......................... 250/339.06, 341.1
  See application file for complete search history.

(56) References Cited

U.S. PATENT DOCUMENTS

| | | | |
|---|---|---|---|
| 4,610,678 A | 9/1986 | Weisman et al. | |
| 4,834,735 A | 5/1989 | Alemany et al. | |
| 4,888,231 A | 12/1989 | Angstadt | |
| 5,260,345 A | 11/1993 | DesMarais et al. | |
| 5,387,207 A | 2/1995 | Dyer et al. | |
| 5,397,316 A | 3/1995 | LaVon et al. | |
| 5,554,145 A | 9/1996 | Roe et al. | |
| 5,569,234 A | 10/1996 | Buell et al. | |
| 5,650,222 A | 7/1997 | DesMarais et al. | |
| 6,004,306 A | 12/1999 | Robles et al. | |
| 7,999,231 B2 | 8/2011 | Iguchi et al. | |
| 2002/0148567 A1* | 10/2002 | Bett et al. | 156/378 |
| 2003/0169424 A1 | 9/2003 | Vogt et al. | |
| 2005/0122531 A1* | 6/2005 | Koele et al. | 356/614 |
| 2008/0033385 A1 | 2/2008 | Grota | |

* cited by examiner

*Primary Examiner* — David Porta
*Assistant Examiner* — Hugh H Maupin
(74) *Attorney, Agent, or Firm* — Charles R. Matson

(57) ABSTRACT

A system for imaging a distribution of an absorbent material within an absorbent article. The system includes a radiation source and a detector positioned such that the absorbent article is situated between the radiation source and the detector. The absorbent article includes an absorbent material having a spatial distribution within the absorbent article. Infrared radiation within a particular wavelength range (e.g., 3 μm to 3.2 μm) is more likely to be absorbed by the absorbent material than by other materials within the absorbent article. The radiation source is configured to generate infrared radiation incident on the absorbent article. The detector is configured to detect a quantity of the infrared radiation within the particular wavelength range that was transmitted through the absorbent article. The radiation source is further configured to generate data indicative of the spatial distribution of the absorbent material based on the detected quantity of the infrared radiation.

18 Claims, 11 Drawing Sheets

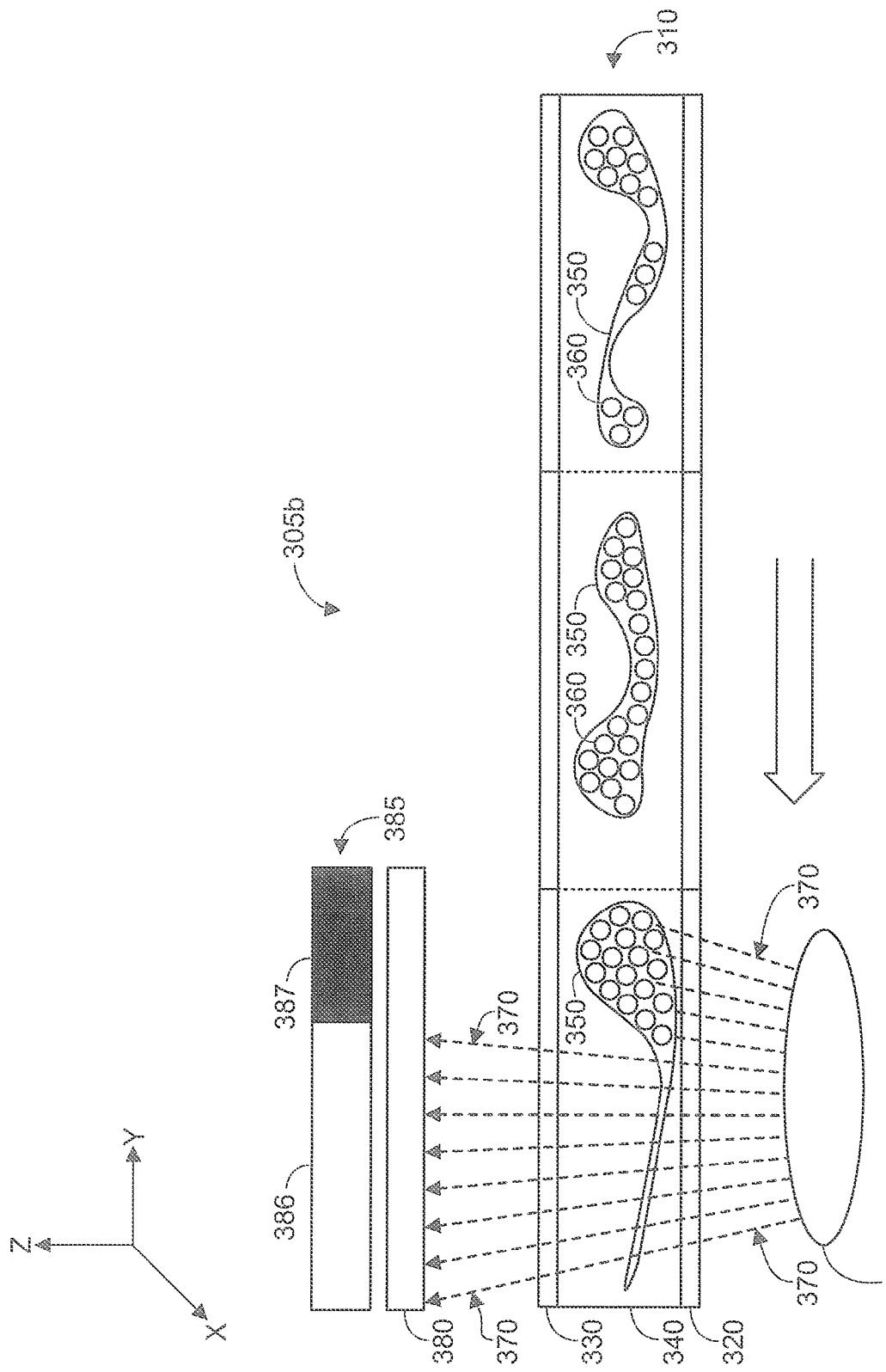

METHOD AND SYSTEM FOR EVALUATING THE DISTRIBUTION OF AN ABSORBENT MATERIAL IN AN ABSORBENT ARTICLE

FIELD OF THE INVENTION

This disclosure relates generally to the field of absorbent articles and, more particularly, to methods and systems for evaluating the distribution of an absorbent material in an absorbent article.

BACKGROUND OF THE INVENTION

An important component of absorbent articles such as diapers, sanitary napkins, pantiliners, incontinent pads, breast pads, perspiration pads, an the like, is an absorbent core structure that includes absorbent materials, such as water-absorbing polymeric particles, typically hydrogel-forming water-swellable polymers, also referred to as absorbent gelling material ("AGM"), or super-absorbent polymers ("SAP"). These absorbent materials ensure that large amounts of fluids, e.g. urine, can be absorbed by the article during its use and locked away, thus providing low rewet and good skin dryness, thereby reducing wearer discomfort.

Different absorbent articles may be designed with different spatial patterns, or distributions, of AGM within their absorbent core structures, depending, for instance, on the nature and/or the intended use of the absorbent articles. For example, diapers intended for boys may have a different distribution of AGM than those intended for girls. Differences in the distributions of AGM may include variations in the shapes of AGM distribution (e.g., rectangular, elliptical, and so on), discrepancies in the overall densities of AGM (or densities in particular regions) and/or in the density transitions between different regions of the absorbent core structure. Differences in the distributions of AGM may further include differences in the absolute quantities of AGM, in the bias, or evenness, of the AGM (e.g., quantity of AGM in the front portion of the absorbent article relative to the back portion). A variety of other factors may contribute to the difference in the distribution of AGM in different absorbent articles, including the amount of AGM laminate, AGM scatter, etc.

Because different absorbent articles may be designed with different spatial distributions of AGM within their absorbent core structures, it is often desired to evaluate the distribution of AGM in a particular absorbent article. For example, the distribution of AGM may be evaluated for quality control purposes during manufacturing (e.g., to ensure that absorbent articles are produced to meet or exceed certain requirements). Additionally, or alternatively, evaluation of the distribution of AGM may be performed in a product and/or process development context, for instance, to develop more optimal techniques for distributing AGM within a particular type of absorbent article.

In the past, distribution of AGM within a given absorbent article could be evaluated in a number of ways. For example, quality control personnel could physically feel for a presence or an absence of AGM in different regions of the absorbent article with their fingers and roughly estimate the distribution of AGM. In some cases, the absorbent article could be passed through some sort of a capacitive sensor, and the amount of AGM in different portions of the absorbent article could be approximated based on the capacitance of the different portions.

The absorbent article could also be cut open, and various sections of the cut-up absorbent article could be examined under a microscope to identify the distribution of AGM in the various sections. The various sections could also be weighed, and the quantity of AGM in each section could be estimated based on the respective weights of the sections.

Traditional methods of evaluating the distribution of AGM in an absorbent article present a number of problems. Results yielded by these methods are typically imprecise, inconsistent, or both. For example, the test that involves physically feeling for the presence or absence of AGM with fingers may yield different results based on who is doing the testing. Furthermore, given that a granule of AGM is roughly the same size as a grain of salt, a person's fingers may not be sensitive enough to provide a sufficiently accurate estimation. The same may be said regarding capacitive sensors.

With regard to methods that involve cutting the absorbent article into several sections, these methods may provide information regarding distribution of AGM among the different sections, but they might not provide helpful information regarding the distribution of AGM within the individual sections. For example, if the absorbent article is cut into three sections, and each section has roughly the same weight, it does not necessarily mean that the AGM is distributed uniformly within each section. Furthermore, cutting up the absorbent article may disrupt the original distribution of AGM and, thus, make it difficult, if not impossible, to determine the original AGM distribution. Still further, cutting up the absorbent article typically means eliminating that absorbent article from production, and that may be undesirable, for example, in the context of an inline manufacturing process.

SUMMARY OF THE INVENTION

The present disclosure provides techniques for evaluating the distribution of an absorbent material in an absorbent article.

In one embodiment, a system for imaging a distribution of an absorbent material within an absorbent article includes a radiation source and a detector. The radiation source and the detector are positioned such that the absorbent article is situated between the radiation source and the detector. The absorbent article includes an absorbent material (e.g., absorbent gelling material (AGM)) having a spatial distribution within the absorbent article. Infrared radiation within a particular wavelength range (e.g., 3 µm to 3.2 µm) is more likely to be absorbed by the absorbent material than by other materials within the absorbent article.

The radiation source is configured to generate infrared radiation incident on the absorbent article. The detector is configured to detect a quantity of the infrared radiation within the particular wavelength range generated by the radiation source that was transmitted through different regions of the absorbent article. The radiation source is further configured to generate data indicative of the spatial distribution of the absorbent material based on the detected quantity of the infrared radiation corresponding to the different regions of the absorbent article.

In various implementations, one or more of the following features may be included. The absorbent article may be an assembled product or a preassembled product. The absorbent article may be a diaper, a sanitary napkin, a pantiliner, an incontinent pad, a breast pad, a perspiration pad, etc.

The radiation source may include multiple light sources configured to transmit the infrared radiation, wherein at least one of the multiple light sources is a tungsten-halogen bulb. The radiation source may further include a diffuser configured to diffuse the infrared radiation transmitted by the multiple light sources to produce a substantially uniform radiation pattern across the absorbent article.

The detector may include a mid wave infrared camera capable of detecting infrared radiation in the particular wavelength range. The detector may further include a filter that substantially blocks infrared radiation outside of the particular wavelength range.

The detector may be further configured to generate an absorbent material distribution image representing the spatial distribution of the absorbent material within the absorbent article based on the data indicative of the spatial distribution of the absorbent material within the absorbent article. A color depth within a given region in the absorbent material distribution image may be indicative of a concentration of the absorbent material in the corresponding region of the absorbent article.

The absorbent material distribution image may be a binary image including a first color and a second color, the first color representing presence of an absorbent granule and the second color representing absence of the absorbent granule. The absorbent material distribution image may also be a grayscale image, where darker grayscale levels represent a higher concentration of absorbent granules and lighter grayscale levels represent a lower concentration of absorbent granules.

In another embodiment, a method for evaluating a distribution of an absorbent material within an absorbent article includes using infrared imaging to generate image data, where the image data represents a spatial distribution of an absorbent material within an absorbent core of the absorbent article. The method further includes transforming the image data into one or more attribute values related to one or more attributes of the spatial distribution of the absorbent material. The method further includes representing the one or more attribute values as output.

In various implementations, one or more of the following features may be included. For example, the method may further include determining a quality of the absorbent article based on the one or more attribute values.

The attributes of the spatial distribution may include, by way of example, a shape of the spatial distribution formed by the absorbent material, a pattern of the spatial distribution formed by the absorbent material, a quantity of the absorbent material within the absorbent core, a density of the absorbent material within the absorbent core, an evenness of the spatial distribution, a location of one or more density transitions within the spatial distribution, a presence of absorbent material laminate, and the presence of islands of absorbent material.

Determining the quality of the absorbent article may include determining a disparity between the determined one or more attributes of the spatial distribution of the absorbent material and a corresponding one or more desired attributes of the spatial distribution of the absorbent material.

In another embodiment, a method of evaluating quality of an absorbent material includes using infrared imaging to generate data indicative of an absorbance of infrared radiation within a particular wavelength range (e.g., 3 μm to 3.2 μm) incident on a target article. The target article includes a monolayer of absorbent material substantially covering a surface of the target article. The infrared radiation within the particular wavelength range is more likely to be absorbed by the absorbent material than by other materials within the target article. The method further includes using infrared imaging to generate data related to an absorbance of infrared radiation within the particular wavelength range incident on an absorbent core of an absorbent article. The method further includes determining a quality of the absorbent article by comparing a disparity between the data related to the absorbance of infrared radiation within the particular wavelength range incident on the target article and the data related to the absorbance of infrared radiation within the particular wavelength range incident on the absorbent core of the absorbent article.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 3B illustrates an example inline AGM distribution imaging system;

Like reference numbers and designations in the various drawings indicate like elements. Furthermore, when individual elements are designated by references numbers in the form Nn, these elements may be referred to in the collective by N. For example, FIGS. 2A and 2B illustrate example AGM distribution imaging systems 200a and 200b, respectively, that may be referred to collectively as AGM distribution imaging systems 200.

DETAILED DESCRIPTION OF THE INVENTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning Finally, unless a claim element is defined by reciting the word "means" and a function without the recital of any structure, it is not intended that the scope of any claim element be interpreted based on the application of 35 U.S.C. §112, sixth paragraph.

Much of the disclosed functionality and many of the disclosed principles are best implemented with or in software programs or instructions and integrated circuits (ICs) such as application specific ICs. It is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation. Therefore, in the interest of brevity and minimization of any risk of obscuring the principles and concepts in accordance to the present invention, further discussion of such software and ICs, if any, will be limited to the essentials with respect to the principles and concepts of the preferred embodiments.

All patents and patent applications (including any patents which issue thereon) assigned to the Procter & Gamble Company referred to herein are hereby incorporated by reference to the extent that it is consistent herewith.

Absorbent Articles and Absorbent Materials

Figure 1A:
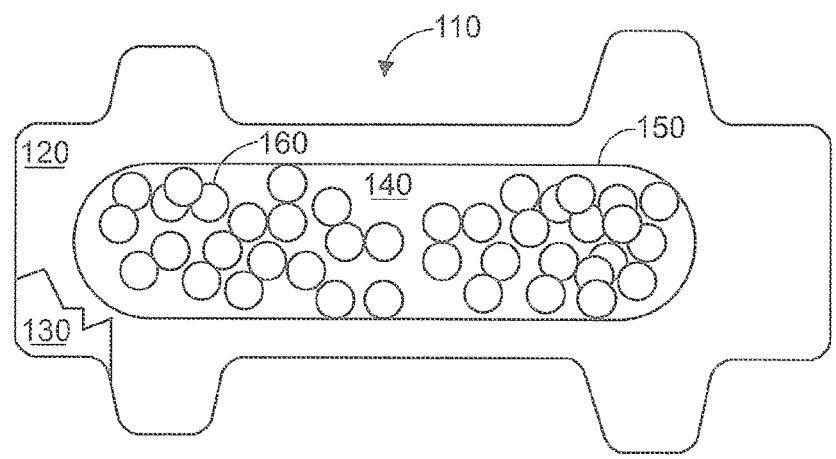
FIG. 1A is a partial aerial view of an the example absorbent article.
Figure 1B:
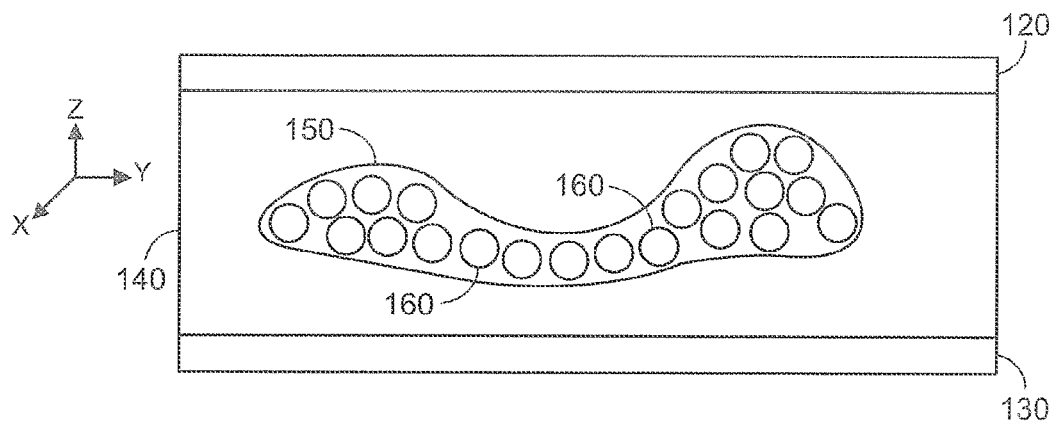
FIG. 1B is a partial cross-section view of an example absorbent article.

FIGS. 1A and 1B illustrate an example absorbent article 110, such as a diaper, a sanitary napkin, a pantiliner, an incontinent pad, a breast pad, a perspiration pad, and so on. FIG. 1A illustrates a partial aerial view of the example absorbent article 110, and FIG. 1B illustrates a partial cross section of the absorbent article. It will be recognized that the system and method of the present invention are not limited to use with standalone fully assembled absorbent articles, but could also be used for absorbent inserts and liners, e.g., a core assembly for a diaper. As used herein, the term "absorbent article" shall therefore be understood as referring to either a fully assembled article or an absorbent component of an article.

The absorbent article 110 generally includes a liquid pervious topsheet 120, a fluid impervious backsheet 130, both of which may be made of nonwoven fabric, and an absorbent core 140 disposed between the topsheet 120 and the backsheet 130. While the topsheet 120, the backsheet 130, and the absorbent core 140 may be assembled in a variety of well-known configurations, various preferred configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The absorbent core 140 may include an absorbent material 150 that is generally compressible, conformable, non-irritating to the wearer's skin, and capable of absorbing and retaining liquids such as urine and other certain body exudates. The absorbent core 140 may include a wide variety of liquid-absorbent materials, including Absorbent Gelling Materials (AGM). AGM may be formed, for example, by superabsorbent polymers, and AGM may include AGM granules (or particles) 160 that can swell upon contact with liquids, such as urine. While the AGM may include AGM granules 160 of various sizes, shapes or forms, such as granular, spherical, flakes, fibrous, etc., the AGM granules 160 are often irregularly shaped particles, having a mean particle size of from 10 µm to 1000 µm, typically with less than 5% by weight having a particle size of less than 5 µm, and with less than 5% by weight having a particle size of more than 1200 µm.

It will be understood by one of ordinary skill in the art that AGM and AGM granules 160 are used herein as just one example of an absorbent material, and that the instant disclosure is not limited to AGM or to any particular absorbent material or materials. Examples of other absorbent materials include creped cellulose wadding; melt blown polymers, including co-form; chemically stiffened, modified or cross-linked cellulosic fibers; tissue, including tissue wraps and tissue laminates; absorbent foams; absorbent sponges; or any other known absorbent material or combinations of materials. Example absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The AGM granules 160 may be distributed within the absorbent core 140 of the absorbent article 110 in a variety of ways to form different patterns and shapes (including irregular shapes) both longitudinally (length wise or x-directionally) and laterally (cross- or y-directionally), but also along the thickness or caliper (or z-direction) of the absorbent article 110. As explained in the background section, there may be various reasons for arranging AGM granules 60 in a particular absorbent article 10 in a special way, depending, for instance, on the nature and/or the intended use of the absorbent article 110. The present disclosure is directed at providing techniques for evaluating the distribution of AGM granules 160 in a given absorbent article.

AGM Distribution Evaluation Overview

Figure 2:
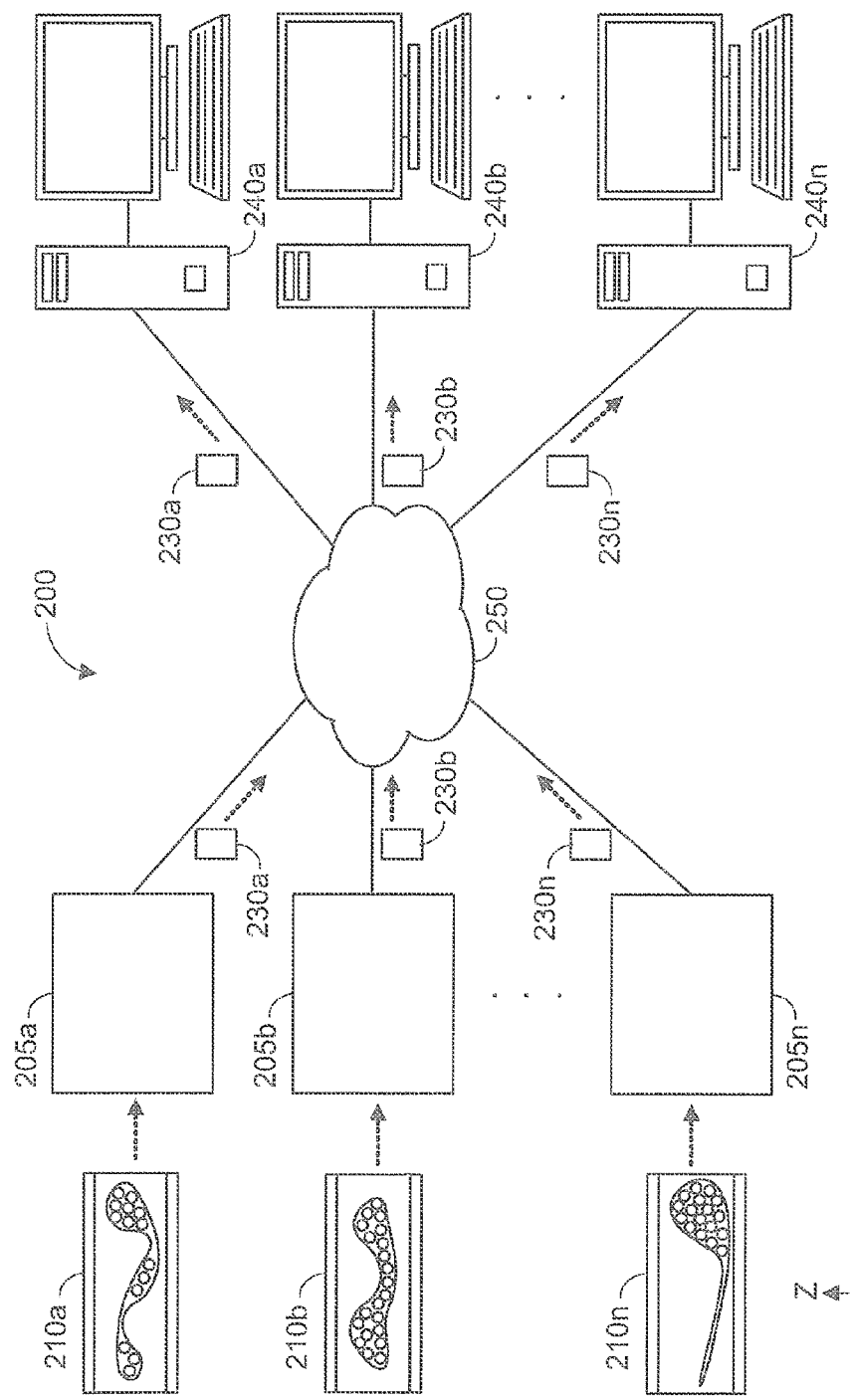
FIG. 2 is a block diagram of an example AGM distribution evaluation system.

FIG. 2 is a block diagram of an example AGM distribution evaluation system 200 for evaluating the distribution of AGM within an absorbent article. For example, the AGM distribution evaluation system 200 may be used to evaluate the distribution of AGM granules in absorbent articles similar to the absorbent article 110 illustrated in FIGS. 1A-1B. It will be understood, however, that the AGM distribution evaluation system 200 may be used to evaluate the distribution of AGM in other types of absorbent articles.

The AGM distribution evaluation system 200 includes one or more AGM distribution imaging systems 205 coupled to one or more AGM distribution image processing systems 240 (e.g., directly, via a network 250). Generally speaking, the AGM distribution imaging systems 205 represent AGM distribution within absorbent articles 210 as image data 230, and the AGM distribution image processing systems 240 generally process the image data 230 to allow users to evaluate the AGM distribution within absorbent articles 210. For example, the AGM distribution image processing systems 240 may simply display (e.g., on a computer screen) the distribution of AGM within a given absorbent article 210 as an image. Alternatively, or in addition, the AGM distribution image processing systems 240 may provide various types of quantitative metrics to the user regarding the AGM distribution.

Details of AGM imaging and AGM image processing will be discussed in reference to FIGS. 3A-12. In particular, some example AGM distribution imaging systems 205 will be discussed in reference to FIGS. 3A-5, and example AGM distribution image processing system 240 will be discussed in reference to FIGS. 6-10.

AGM Distribution Imaging

Figure 3A:
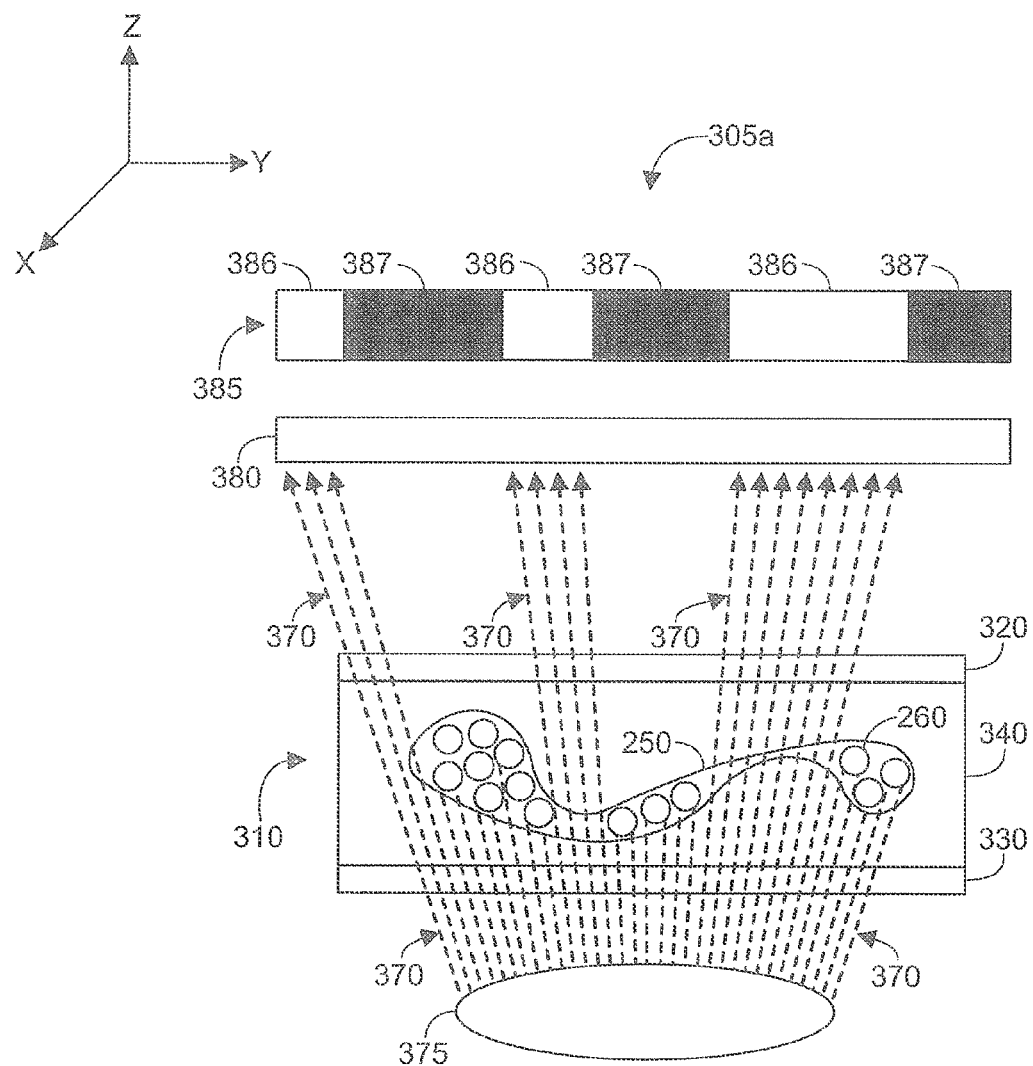
FIG. 3A illustrates an example standalone AGM distribution imaging system.

FIGS. 3A and 3B illustrate example AGM distribution imaging systems 305a and 305b, respectively, that may be referred to collectively as example AGM distribution imaging systems 305. The AGM distribution imaging systems 305a and 305b may be used as AGM distribution imaging systems 205 illustrated in FIG. 2. However, it will be understood that the AGM distribution evaluation system 200 may utilize other AGM distribution imaging systems 205. Furthermore, it will be appreciated that the AGM distribution imaging systems 305a and 305b may be used with systems and devices other than those illustrated in FIG. 2.

Generally speaking, the AGM distribution imaging system 305 includes one or more radiation sources 375 that generate infrared radiation 370 incident on an absorbent article 310 (oriented length-wise or width-wise with respect to the Y-axis) and one or more detectors 380 on the opposite side of the absorbent article 310 that detect the infrared radiation 370 which passes through the absorbent core 340 of the absorbent article 310. The wavelength range of the infrared radiation 370 may be selected such that the infrared radiation 370 may be substantially absorbed by the AGM granules 360 within the absorbent core 340 of the absorbent article 310 but such that the infrared radiation 370 may be substantially transmitted through other materials within the absorbent article 310. In other words, the wavelength range of interest is one in which the infrared radiation 370 is more likely to be absorbed by the absorbent material than by other materials within the absorbent article. As a result, the concentration of AGM granules 360 within a given region of the absorbent core 340 is related to the amount of the infrared radiation 370 (within the wavelength range of interest) that gets absorbed as it passes through that region.

In some embodiments, the wavelength range of interest may be between 3 μm and 3.2 μm, as it has been observed that the absorbance of AGM granules 360 within that wavelength range is higher than the absorbance of other materials in the absorbent article 310 in that range. Accordingly, the radiation source 375 may include one or more sources of infrared radiation that transmit infrared signals through the absorbent article 310, and the detector 380 may include one or more infrared detectors capable of detecting the infrared radiation within the wavelength range of interest on the opposite side of the absorbent article 310. More specifically, the detector 380 may observe the number of photons that are transmitted through different regions of the absorbent core 340. Those regions of the absorbent core 340 that include a higher concentration of AGM granules 360 may absorb more photons, and those regions of the absorbent core 340 that include a lower concentration of AGM granules 360 may absorb fewer photons.

Based on the detected number of photons that pass through the different regions of the absorbent core 340, the detector 380 may generate an AGM distribution image 385, or data related thereto, that represents pictorially the concentration of AGM granules 360 in the corresponding regions. In other words, the AGM distribution image 385 may represent a two-dimensional spatial distribution of AGM granules 360 within the absorbent core 340.

It should be noted that although the detector 380 is illustrated in FIGS. 3A-3B as a single element, the detector 380 may include multiple detector elements. For instance, in some embodiments, the detector 380 may include an array of infrared detector elements.

In general, the distribution of AGM granules 360 in the various regions of the absorbent article 310 may be represented in the AGM distribution image 385 by the color depth in the corresponding region of the AGM distribution image 385. In some embodiments, the color depth, or, more generally, the intensity of a pixel (or a group of pixels) within a particular region of the AGM distribution image 385 may be related to the number of photons transmitted through the corresponding region in the absorbent core 340 and detected by the detector 380. For example, if relatively few photons are transmitted through a given region of the absorbent core 340 and detected by the detector 380 (indicating a relatively high concentration of AGM granules 360), the pixels in the corresponding region of the AGM distribution image 385 may be set to a relatively dark color. Likewise, if a relatively high number of photons is transmitted through a given region of the absorbent core 340 and detected by the detector 380 (indicating a relatively low concentration of AGM granules 360), the pixels in the corresponding region of the AGM distribution image 385 may be set to a relatively bright color. Accordingly, darker sections of the AGM distribution image 385 may correspond to regions within the absorbent core 340 having a higher concentration of AGM granules 360, and lighter sections of the AGM distribution image 385 may correspond to regions within the absorbent core 340 having a lower concentration of AGM granules 360.

It will be appreciated by one of ordinary skill in the art that various types of color palettes may be used for the AGM distribution image 385. In general, however, it may be useful to select a color palette that corresponds to the color depth perception of a human eye. That is, it may be desired to generate an image with a granularity of color depth that a user is able to perceive. This may be achieved in a variety of ways, as discussed blow.

In the example AGM distribution imaging systems 305a-b illustrated in FIGS. 3A and 3B, the AGM distribution image 385 is a binary (e.g., black-and-white) image, where one color (e.g., black) indicates presence, or a relatively high concentration, of AGM granules 360 and another color (e.g., white) indicates absence, or a relatively low concentration, of AGM granules 360. In some embodiments, a threshold for the number of received photons may be selected (e.g., 2170 photons per pixel) below which an AGM granule 360 is indicated to be present (and the corresponding pixel or pixels are set to one color, e.g., black) and above which an AGM granule 360 is indicated to not be present (and the corresponding pixel or pixels are set to another color, e.g., white).

Additionally, or alternatively, the AGM distribution image 385 may be a grayscale (or monochrome) image, in which darker (but not necessarily black) sections generally indicate sections of relatively high concentration of AGM granules 360 and brighter (but not necessarily white) sections 386 generally indicate sections of a relatively low concentration of AGM granules 360. A "gray-area" range in the number of received photons may be determined (e.g., 2142 to 2397 photons per pixel), within which it may be unclear whether AGM granules 360 are present, but below which AGM granules 360 are indicated to be present, and above which AGM granules 360 are indicated not to be present. Consequently, if the number of received photons is lower than the lower limit of the determined gray-area range, the corresponding pixel or pixels may be set to black; if the number of received photons is higher than the upper limit of the determined gray-area range, the corresponding pixel or pixels may be set to white; and if the number of received photons is within the determined gray-area range, the corresponding pixel or pixels may be set to a grayscale level corresponding to the number of received photons relative to the gray-area range.

In some embodiments, the grayscale level corresponding to the number of received photons relative to the gray-area range may be a linear function of the position within the range. For example, if the gray-area range is between X and Y photons, and Z photons were received, the grayscale level may be a linear function of quantities such as $Z/(Y-X)$, $(Y-X)/Z$, and variations thereof. In some embodiments the grayscale level may increase by one level for each additional equal-sized group of received photons. Accordingly, the color palette of the AGM distribution image 385 may correspond to the gray-area range associated with the number of received photons.

It will be appreciated by one of ordinary skill in the art that the number of photons received by the detector 380 in different regions (and the associated distribution of AGM granules 360) may be represented by various other types of AGM distribution images with a range of other color schemes. For example the AGM distribution image 385 may be a colorized grayscale image, or a false-color image, in which the number of received photons may be mapped to a false color palette. The AGM distribution image 385 may also be a sepia-tone image, a duotone, a cyanotype, one of a range of possible monochrome images other than a gray-scale image, etc., in which various visual indicators represent the color depth of the image. The AGM distribution image 385 may also be any other type of a color image in which various color schemes may represent the color depth of the image and the corresponding distribution of AGM granules 360. Still further, the AGM distribution image 385 may distinguish presence of an AGM granule 360 (or a high concentration thereof) from absence of an AGM granule 360 (or absence thereof) via visual indicia, or a visual state, that is not related to color. One example of such an indicia is concentration of particular characters (e.g., to represent high concentration of AGM 350).

Throughout the present disclosure, the terms "visual state" and "visual indicia" refer to an appearance which can be perceived by an unaided human with normal vision. A visual state, or visual indicia, can generally include one or more colors, variations of color(s), patterns, letters, numbers, symbol, designs, images, and/or other visual devices. Colors include well known colors such as red, orange, yellow, green, blue, purple, etc. Variations of a color include variations in chroma, hue, and brightness, among others. While these informal terms are used for ease of reference, embodiments of the present disclosure are intended to encompass all colors which can be perceived by an unaided human with normal vision.

As one example, an unaided human with normal vision should be able to recognize blue and yellow as different colors on sight. Thus, the blue and the yellow would be considered visually distinguishable visual states or visual indicia. As another example, an unaided human with normal vision may be able to recognize a light shade of orange and a dark shade of orange as different shades of a color on sight. Thus, the light shade of orange and the dark shade of orange would be considered visually distinguishable visual states of visual indicia. As a further example, an unaided human with normal vision may be able to recognize a first pattern and a second pattern as different visual states on sight. Thus, the first pattern and the second pattern would be considered visually distinguishable visual states.

As a still further example, an unaided human with normal vision should be able to recognize an area with letters and a blank area as different visual states on sight. Thus, the area with letters and the blank area would be considered visually distinguishable visual states. Similarly, an area with numbers, symbols, designs, images, and/or other visual devices would also be considered visually distinguishable from a blank area or from a uniformly colored area. In addition to these examples, there are many other possible visually distinguishable visual states, as will be understood by one or ordinary skill in the art.

Referring again to FIGS. 3A-3B, it should be noted that unlike conventional systems for evaluating the distribution of AGM 350 within absorbent articles 310, such as those systems that employ capacitive sensors, the example AGM distribution imaging systems 305a-b illustrated in FIGS. 3A and 3B may be used, in some embodiments, to determine presence or absence of individual AGM granules 360. Moreover, because the image 385 representing the distribution of AGM granules 360 may be stored in a digital format (e.g., bitmap, JPEG, TIFF, and so on), various image processing algorithms (e.g., implemented using computer code) may be used to determine a range of quantitative metrics associated with the distribution of AGM granules 360 within an absorbent article 310, as will be subsequently described in more detail.

It should further be noted that the example AGM distribution imaging system 305 allows imaging of the distribution of AGM granules 360 within an absorbent article 310 without physically altering the absorbent article 310 (e.g., cutting it open) and possibly altering the AGM distribution within it. Consequently, as compared to existing systems, the example AGM distribution imaging system 305 provides a more accurate representation of the distribution of AGM 350 within the absorbent article 310 in a non-destructive and non-disturbing manner.

Still further, it should be understood that the example AGM distribution imaging system 305 may be a stand-alone, e.g., offline, system, such as the example AGM distribution imaging system 305a illustrated in FIG. 3A, but the example AGM distribution imaging system 305 may also be part of an inline product assembly system, such as the example AGM distribution imaging system 305b illustrated in FIG. 3B. As a result, the distribution of AGM granules 360 within the absorbent article 310 may be imaged while the absorbent article is in motion, e.g., as it passes through the AGM distribution imaging system 305 on an assembly, or a production line. Moreover, AGM distribution imaging may be performed on multiple absorbent articles 310 as the absorbent articles physically move through the inline assembly system, both in assembled and in preassembled forms.

In an inline production environment, as illustrated in FIG. 3B, each absorbent article 310 may be imaged using the same or different combinations of radiation sources 375 and detectors 380. In some embodiments, a given absorbent article 310 may be imaged more than once, e.g., at different spatial orientations. In some cases, in order to achieve greater consistency across multiple absorbent articles 310, the multiple absorbent articles 210 that are imaged may be exposed to infrared radiation from the radiation source 375 for approximately the same amount of time. Alternatively, in some cases, it may be beneficial to expose different absorbent articles to infrared radiation for different durations of time.

Figure 4:
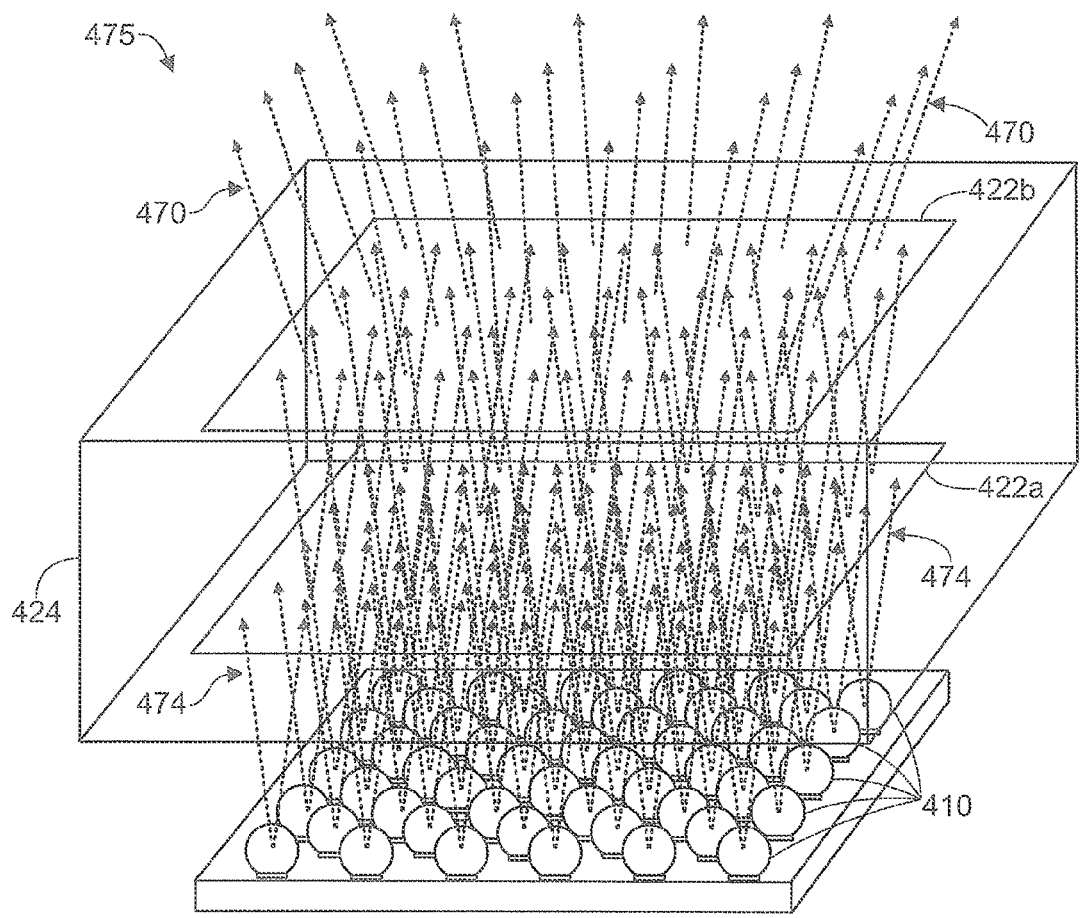
FIG. 4 is a block diagram of an example radiation source.

FIG. 4 is a block diagram of an example radiation source 475 that may be used to generate infrared radiation incident to an absorbent article in order to evaluate the distribution of AGM within the absorbent article. The radiation source 475 may be used as the radiation source 375 in FIGS. 3A-3B. However, it will be understood that the AGM distribution imaging systems 305*a-b* may use a different radiation source 375. Furthermore, although, for ease of explanation, FIG. 4 will be described with reference to FIGS. 1-3B, it will be understood that the example radiation source 475 may be utilized with systems, devices, and absorbent articles other than those illustrated in FIGS. 1-3B.

The radiation source 475 may include a collection of light sources 410 that generate infrared light 474. A number of different light sources 410 may be used including those known in the art. Because it is preferable that different AGM granules (e.g., inside a given absorbent article or inside different absorbent articles evaluated at different points in time) be illuminated by similar radiation 470, it may generally be desired that these light sources 410 produce substantially uniform infrared light 474 over time. Additionally, or alternatively, it may be preferable that the light sources 410 have adjustable level of infrared light 474, e.g., so that the light sources 410 may be calibrated if changes in time do occur, if their position and/or orientation is changed, and so on.

One example of a light source 410 that may produce substantially uniform infrared light 474 over time and that may be adjustable is a broad-spectrum tungsten-halogen bulb. Generally speaking, a tungsten-halogen bulb is an incandescent bulb in which a tungsten filament is sealed into a compact transparent envelope filled with an inert gas and a small amount of halogen such as iodine or bromine. The halogen cycle increases the lifetime of the bulb and prevents its darkening by redepositing tungsten from the inside of the bulb back onto the filament.

Because it may be of interest to evaluate the degree to which AGM granules within different regions of an absorbent article absorb the infrared light 474 produced by the light sources 410, such as tungsten-halogen bulbs, it may further be desired that the material (e.g., glass) enclosing the tungsten filament does not substantially absorb the produced infrared light 474. Accordingly, in some embodiments, it may be preferable to use tungsten-halogen bulbs that have relatively thin glass structures enclosing the tungsten filament.

The light sources 410 may be arranged and generally operated in a variety of ways. For example, the light sources 410 may be arranged in a two-dimensional pattern, such as a rectangular grid (e.g., roughly 26 inches by 12 inches). The light sources 410 may also be arranged as a staggered array, or checkered, as illustrated in FIG. 4, to provide a more uniform distribution of the infrared light 474. In some embodiments, the light sources 410 may be operated between 4 and 24 volts (e.g., 7 or 8 volts). The number of light sources 410 may vary, including 28, 50, 58, or any other number of different tungsten-halogen bulbs.

Because it is generally preferable that different AGM granules in different regions of the absorbent article be illuminated by similar radiation 470, at least within a spectrum of interest (e.g., corresponding to wavelengths between 3 μm and 3.2 μm), it may further be desired that the radiation source 475 scatter the light and produce substantially uniform radiation 470 in space. Accordingly, in some embodiments, a diffuser assembly 424 may be used to generally diffuse the light 474 generated by the collection of individual light sources 410 to produce a substantially uniform radiation 470 across the absorbent article.

Various diffuser assemblies may be used in the radiation source 475. For example, the diffuser assembly 424 may include one or more (e.g., two) quartz diffusers 422 situated between the light sources 410 and the absorbent article and oriented substantially parallel to the absorbent article and to the plane of the light sources 410, as illustrated in FIG. 4. One example of a suitable quartz diffuser 422 is the low O-H quartz diffuser manufactured by Point Source Inc. of Germantown, Ohio, part number PSPG98745.

In some embodiments, the diffuser assembly 424 may include one quartz diffuser 422*a* close to the light sources 410 (e.g., less than an inch away from the light sources), and another quartz diffuser 422*b* farther away from the light sources (e.g., 4-6 inches away from the light sources 410). Each quartz diffuser 422 may be made of GE 124 quartz material and have a rectangular shape with a length of 25.7 inches, a width of 11.4 inches, and a height (or thickness) of 0.118 inches. However, in some embodiments, or in some modes of operation, other materials, shapes and dimensions of the quartz diffusers 422 may be suitable. Also, more or fewer quartz diffusers 422 may be used.

Figure 5:
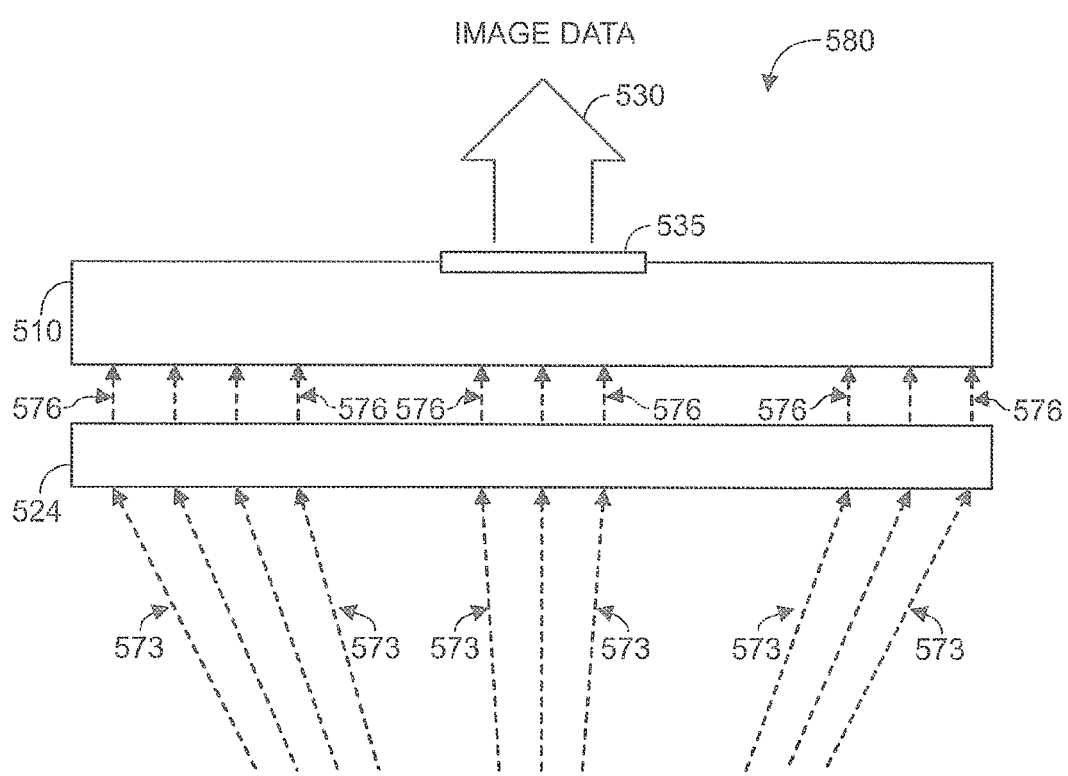
FIG. 5 is a block diagram of an example detector.

FIG. 5 is a block diagram of an example detector 580 that may be used to detect infrared radiation 573 that passes through an absorbent article in order to generate an image representing the distribution of AGM granules within the absorbent article. The detector 580 may be used as the detector 380 in FIGS. 3A-3B. However, it will be understood that the AGM distribution imaging systems 305*a-b* may use a different detector 380. Furthermore, while for ease of explanation FIG. 5 will be described with reference to FIGS. 1-4, it will be understood that the example detector 580 may be utilized with systems, devices, and absorbent articles other than those illustrated in FIGS. 1-5.

The detector 580 includes a mid wave infrared (e.g., thermal) camera 510 that is configured to detect infrared radiation 573 that passes through an absorbent article, e.g., portion of the infrared ration 470 generated by the radiation source 475 illustrated in FIG. 4 that is not absorbed by the absorbent article. As discussed above, the wavelength range of the infrared radiation 573 that is of particular interest is that within which the infrared radiation 573 is absorbed by AGM granules, e.g., infrared radiation 573 with wavelengths roughly between 3 and 3.2 μm. Accordingly, it may be desired that the mid wave infrared camera 510 be particularly sensitive and responsive to infrared radiation within that region of 3 to 3.2 μm. Furthermore, because the mid wave infrared camera 510 may be required to detect infrared radiation passing through an absorbent article as the absorbent article is moving along, for example, an assembly line, it may further be desired that the mid wave infrared camera 510 have a suitably high frame rate. An example of a suitable mid wave infrared camera 510 would be an infrared camera that has a sensitivity range between 3 μm and 5 μm and a frame rate of 120 frames per second for a 640×512 resolution and 424 frames per second for a 305×256 resolution.

In addition to having the capability to detect infrared radiation passing through an absorbent article and generating an image representing the distribution of AGM granules within that absorbent article, the mid wave infrared camera 510 may include one or more communication interfaces 535 to communicate image data 530, e.g., to an AGM distribution image processing system, such as the AGM distribution image processing system 640 described below in reference to FIG. 6, or more generally, to attached computers, remote servers and other devices. These communication interfaces 535 may include analog interfaces, digital interfaces, Gigabit Ethernet interfaces, and so on. The mid wave infrared camera 510 may include additional components that, for ease of explanation, are not shown in FIG. 5, including those that are common, for example, to computing devices. For instance, the mid wave infrared camera 510 may include memory storage space for storing the generated AGM distribution images, various user interfaces to enable a user to interact with the mid wave infrared camera 510, etc. The mid wave infrared camera 510 may further include various software for data acquisition, analysis, reporting, and so on.

One particular example of a suitable mid wave infrared camera 510 is the ThermoVision® SC6000 infrared camera ("SC6000 camera") manufactured by FLIR Systems, Inc. The SC6000 camera supports simultaneous and independent analog and digital output data streams. The SC6000 camera also supports adjustable integration times (9 µs to full frame) and adjustable integration rates (120 frames per second for a 640×512 resolution and 424 frames per second for a 305×256 resolution). The frame rate is suitably high to make the SC6000 camera capable of detecting infrared radiation passing through an absorbent article while the absorbent article is moving along an assembly line, for instance.

It should be understood that the SC6000 camera is only one type of a suitable mid wave infrared camera 510. Other devices may be used to detect infrared radiation passing through an absorbent article and to generate an image representing the distribution of AGM granules within that absorbent article, including various scanning devices, focal plane arrays, linear arrays, line scans, and so on.

In addition to the mid wave infrared camera 510, the detector 580 may include an optical band pass filter 524 for substantially blocking, or filtering out, the infrared radiation that is outside the wavelength range of interest. For example, the optical band pass filter 524 may pass infrared radiation 576 that, if passed through AGM, would get substantially absorbed by AGM granules.

One example of a suitable optical filter 524 is an optical filter manufactured by Barr Associates Inc. and sold under lot no. 1105072016-2. This filter has a peak transmittance of 95.1% and an effective span from 2.7581 to 3.3752 µm. Of course, other suitable filters may be used.

AGM Distribution Image Processing

Referring again to FIG. 2, once an AGM distribution imaging system 205 (such the AGM distribution imaging system described in reference to FIGS. 3-5) represents the AGM distribution of an absorbent article as AGM distribution image data 230, the AGM distribution image data 230 may be communicated to one or more AGM distribution image processing systems 240. An AGM distribution image processing system 240 may then process the AGM distribution image data 230 to allow users to evaluate the AGM distribution within the absorbent article 210.

Figure 6:
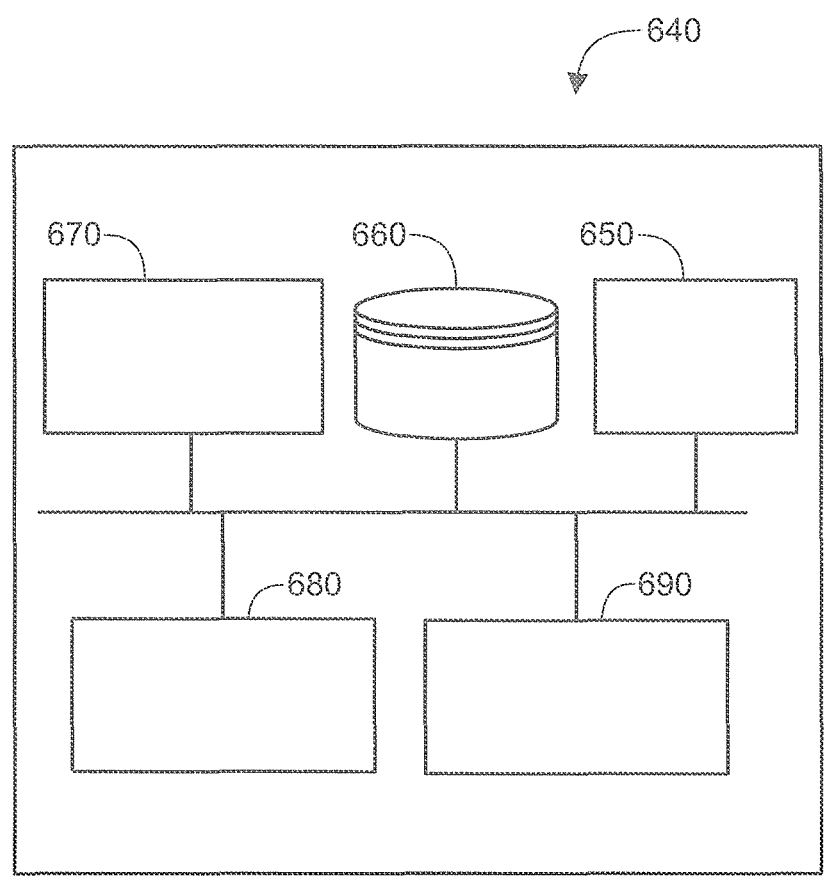
FIG. 6 is a block diagram of an example AGM distribution image processing system 640.

FIG. 6 is a block diagram of an example AGM distribution image processing system 640. The example AGM distribution image processing system 640 may be used as one of the AGM distribution image processing system 240 in the AGM distribution evaluation system 200 illustrated in FIG. 2. However, it will be understood that the AGM distribution evaluation system 200 may use other AGM distribution image processing system 240. Furthermore, for ease of explanation, the example AGM distribution image processing system 640 will be described with reference to FIGS. 1-5. However, it will be understood that the example AGM distribution image processing system 500 may be utilized with systems, devices, and absorbent articles other than those illustrated in FIGS. 1-5.

The AGM distribution image processing system 640 may include a number of units, or components. For example, AGM distribution image processing system 640 may include an image collector 650 for collecting image data from various AGM distribution imaging systems (e.g., the AGM distribution imaging system 205 illustrated in FIG. 2 or the AGM distribution imaging system described in reference to FIGS. 3-5) and an image database 660 for storing the image data. In order to interact with the various AGM distribution imaging systems, the AGM distribution image processing system 640 may further include a communication interface 670. Still further, the AGM distribution image processing system 640 may include an AGM distribution image processing application 680 that is generally configured to process the collected AGM distribution image data and represent as output (e.g., via a user interface 690) quality values associated with the distribution of AGM granules in absorbent articles corresponding to that image data. In some embodiments, in order to perform some of the image processing functions, the AGM distribution image processing application 680 may interact with other applications, including those known in the art, such as the FLIR Software Development Kit (SDK) manufactured by FLIR Systems, Inc., LabView manufactured by National Instruments, Vision Builder for Automated Inspection (VBAI) manufactured by National Instruments, and various others.

It should be understood that the AGM distribution image processing system 640, in some embodiments, or in some modes of operation, may not include one or more of the units 650-680 described above or, alternatively, may not use each of the units 650, 660, 670, 680, 690 in processing AGM distribution image data. Furthermore, it will be appreciated that, if desired, some of the units 650, 660, 670, 680, 690 may be combined, or divided into distinct units.

Figure 7:
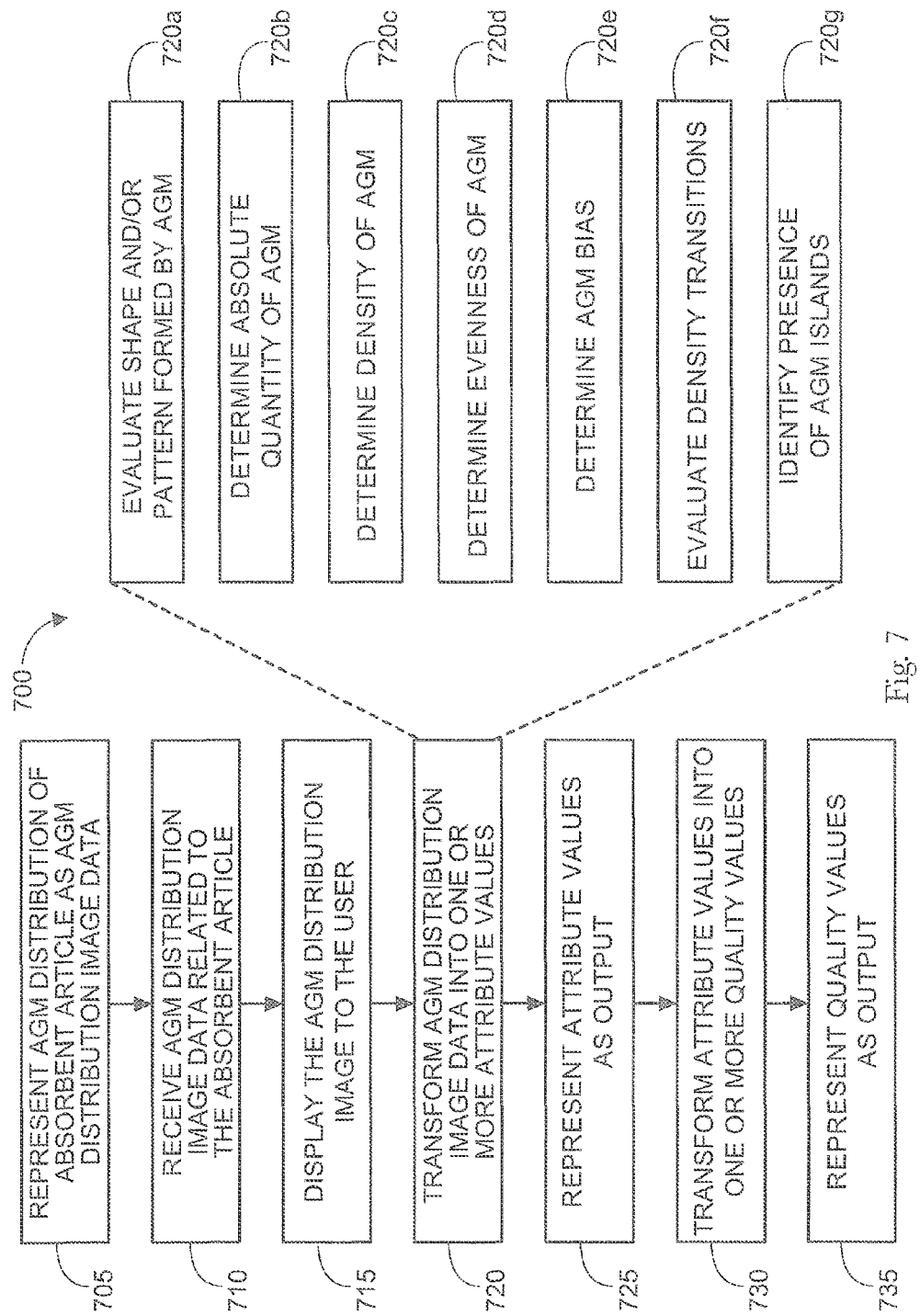
FIG. 7 is a flow diagram illustrating an example method for processing AGM distribution image data.

FIG. 7 is a flow diagram illustrating an example method 700 for processing AGM distribution image data using an AGM distribution image processing system, such as the AGM distribution image processing system 640 illustrated in FIG. 6. For ease of explanation, FIG. 7 will be described with reference to FIGS. 1-6. It will be understood, however, that the example method 700 for processing AGM distribution image data may be utilized with systems, devices and absorbent articles other than those illustrated in FIGS. 1-6.

Once an AGM distribution imaging system (such the AGM distribution imaging system described in reference to FIGS. 3-5) represents the AGM distribution of an absorbent article as AGM distribution image data (block 705), the AGM distribution image processing system 640 may use the communication interface 670, the AGM distribution image processing application 680, and/or the image collector 650 to receive, or retrieve the AGM distribution image data (block 710). If desired, the AGM distribution image represented by the received AGM distribution image data may be displayed to the user (block 715) to allow the user to inspect the AGM distribution image visually and determine and/or evaluate various attributes of the AGM distribution within the absorbent article. Alternatively, or in addition, the AGM distribution image processing application may be used to transform the AGM distribution image data into one or more AGM distribution attribute values (block 720).

For example, in some embodiments, the AGM distribution image processing application may be used to transform the AGM distribution image data into one or more AGM distribution attribute values related to the shape and/or pattern formed by the AGM granules (block 720*a*). The AGM distribution attribute values related to the shape and/or pattern formed by the AGM granules may be indicative of the perimeter, or the area within the absorbent core that is covered by the AGM granules. Additionally, or alternatively, the AGM distribution attribute values related to the shape and/or pattern formed by the AGM granules may indicate the lengths of the different sides of the AGM pattern. The AGM distribution attribute values related to the shape and/or pattern formed by the AGM granules may correspond to other metrics indicative of the shape and/or pattern formed by the AGM granules, such as perimeter-to-length ratios.

In some embodiments, the AGM distribution image processing application may be used to transform the AGM distribution image data into one or more AGM distribution attribute values related to the quantity of the AGM within the absorbent core of the absorbent article (block 720*b*).

For instance, the AGM distribution attribute values related to the quantity of the AGM may be indicative of the number of individual AGM granules in the absorbent core. However, other quantity metrics (e.g., surface area or volume covered by the AGM granules) may be used. Also, the AGM distribution attribute values related to the quantity of the AGM may be indicative of the quantity of AGM within a particular region, or regions, within the absorbent core, or of the quantity of AGM within the absorbent core as a whole.

In some embodiments, the AGM distribution image processing application may be used to transform the AGM distribution image data into one or more AGM distribution attribute values related to the density of the AGM within the absorbent core of the absorbent article (block 720*c*). Similar to the AGM distribution attribute values related to the quantity of the AGM, the AGM distribution attribute values related to the density of the AGM may be indicative of the density of AGM within a particular region, or regions, within the absorbent core, or of the density of AGM within the absorbent core as a whole. For example, it may be desired to transform the AGM distribution image data into one or more AGM distribution attribute values related to the density of the AGM within regions that are more likely to come in contact with fluids.

In some embodiments, the AGM distribution image processing application may be used to transform the AGM distribution image data into one or more AGM distribution attribute values related to the evenness of the AGM within the absorbent core of the absorbent article (block 720*d*). For example, AGM distribution attribute values related to the evenness of the AGM within the absorbent core of the absorbent article may be indicative of how uniformly the AGM granules are distributed within the absorbent core, or within a particular region of the absorbent core.

In some embodiments, the AGM distribution image processing application may be used to transform the AGM distribution image data into one or more AGM distribution attribute values related to the AGM bias within the absorbent core of the absorbent article (block 720*e*). For example, AGM distribution attribute values related to the AGM bias within the absorbent core of the absorbent article may indicate whether there is more AGM at the front of the absorbent article than in the back, on one side than on another, in the center of the absorbent core than on the periphery, and so on.

In some embodiments, the AGM distribution image processing application may be used to transform the AGM distribution image data into one or more AGM distribution attribute values related to density transitions in AGM within the absorbent article (block 720*f*). For example, the AGM distribution attribute values related to density transitions in AGM within the absorbent article may simply indicate existence of density transitions in AGM. Additionally, or alternatively, the AGM distribution attribute values related to density transitions in AGM within the absorbent article may indicate the regions within the absorbent core with density transitions in AGM and/or the rate of change in the density of AGM in the various regions.

In some embodiments, the AGM distribution image processing application may be used to transform the AGM distribution image data into one or more AGM distribution attribute values related to presence of AGM islands within the absorbent article (block 720*g*). Similarly, the AGM distribution image processing application may be used to transform the AGM distribution image data into one or more AGM distribution attribute values indicating regions within the absorbent core that have little or no AGM.

The AGM distribution image processing application may be used to transform the AGM distribution image data into one or more AGM distribution attribute values related to various other attributes of the distribution of AGM within the absorbent article (e.g., the degree of scatter of the AGM granules). Alternatively, in some embodiments, the AGM distribution image processing application may be used to transform the AGM distribution image data into only a subset of the AGM distribution attribute values described above. Furthermore, it will be understood that the AGM distribution image processing application need not transform the AGM distribution image data into one or more AGM distribution attribute values in any particular order.

Once the AGM distribution image processing application transforms the AGM distribution image data into one or more AGM distribution attribute values (block 720), the AGM distribution image processing application may represent the AGM distribution attribute values as output (block 730). For example, the AGM distribution image processing application may present the AGM distribution attribute values to the user, e.g., via a user interface, such as the user interface 690 illustrated in FIG. 6. Additionally, or alternatively, the AGM distribution image processing application may store the AGM distribution attribute values in a file, communicate the AGM distribution attribute values to other systems, and so on.

In some embodiments, the AGM distribution image processing application may further transform the AGM distribution attribute values into one or more AGM distribution quality values indicative of the quality of the AGM distribution within the absorbent article (block 735). Thus, the AGM distribution image processing application may enable a user to determine the quality of the AGM distribution within the absorbent article based on one or more attributes of the AGM distribution within the absorbent article. For instance, the AGM distribution image processing application may represent the AGM distribution quality values as output (block 740), e.g., by present the AGM distribution quality values to the user via a user interface (such as the user interface 690 illustrated in FIG. 6). Alternatively, the AGM distribution image processing application may present to the user only the AGM distribution attribute values (and not the AGM distribution quality values), and the user may determine the AGM distribution quality manually, e.g., by comparing the presented AGM distribution attribute values to the desired AGM distribution attribute values.

Evaluation of AGM Monolayer in an Absorbent Article

In some cases, the quality of the absorbent article, or an absorbent component of an article yet to be fully assembled, may be related to the presence of a monolayer of AGM granules within the absorbent core of the absorbent article or within a particular region of the absorbent article. Accordingly, it may be, at times, desired to use an AGM distribution evaluation system, such as the AGM distribution evaluation system 200 illustrated in FIG. 2 to characterize an AGM monolayer and to evaluate the AGM monolayer in absorbent articles.

Figure 8A:
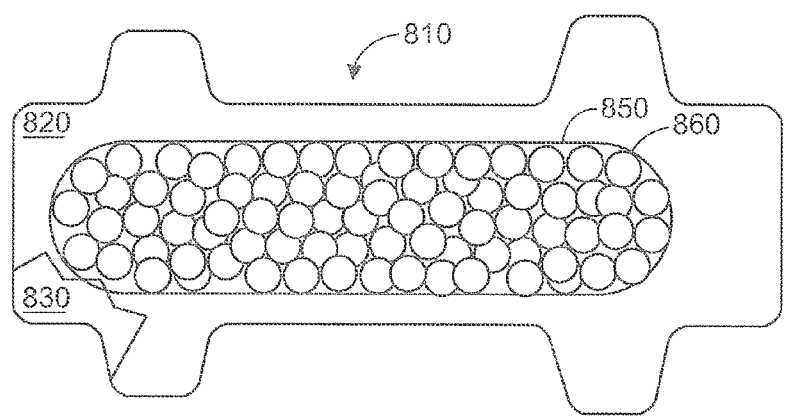
FIG. 8A is a partial aerial view of an example absorbent article with an AGM monolayer.
Figure 8B:
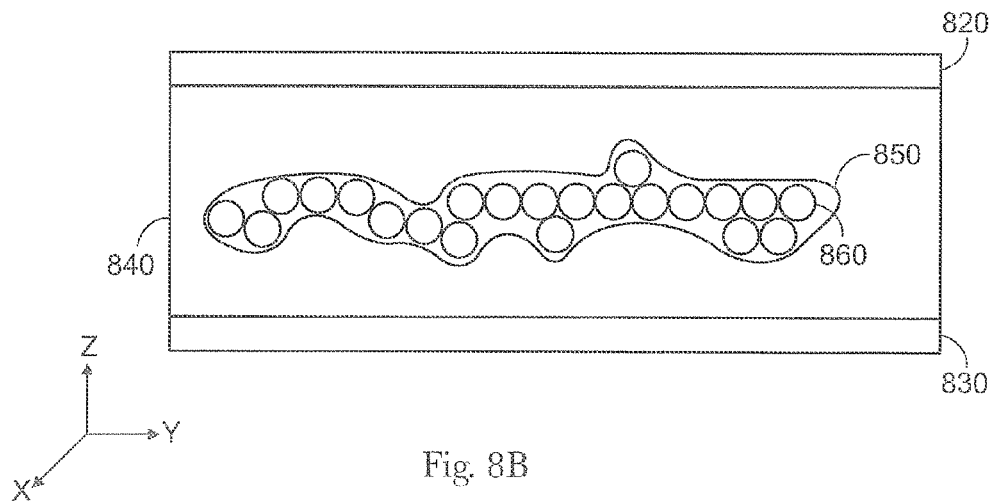
FIG. 8B is a partial cross-section view of an example absorbent article with an AGM monolayer.

FIGS. 8A and 8B illustrate an example absorbent article 810, such as a diaper, a sanitary napkin, a pantiliner, an incontinent pad, a breast pad, a perspiration pad, and so on, that includes an AGM monolayer 850 in the absorbent core 840. FIG. 8A illustrates a partial aerial view of the example absorbent article 810, and FIG. 8B illustrates a partial cross section of the absorbent article 810.

Generally speaking, an article (such as the absorbent article 810) is said to include an AGM monolayer when the article includes a surface that is substantially covered by at least one layer of AGM granules 860, but not necessarily more than one AGM granule 860 over any of the surface area. The AGM monolayer within an absorbent article 810 may therefore substantially ensure, or make it highly likely, that the topsheet 820 and the backsheet 830 of the absorbent article 810 do not come in contact with each other. More particular requirements as to what constitutes an AGM monolayer 850 (e.g., spacing of adjacent AGM granules 860, minimum number of AGM granules per unit of surface area, and so on) may depend on various factors, such as the nature and/or the intended use of the absorbent article.

Figure 9:
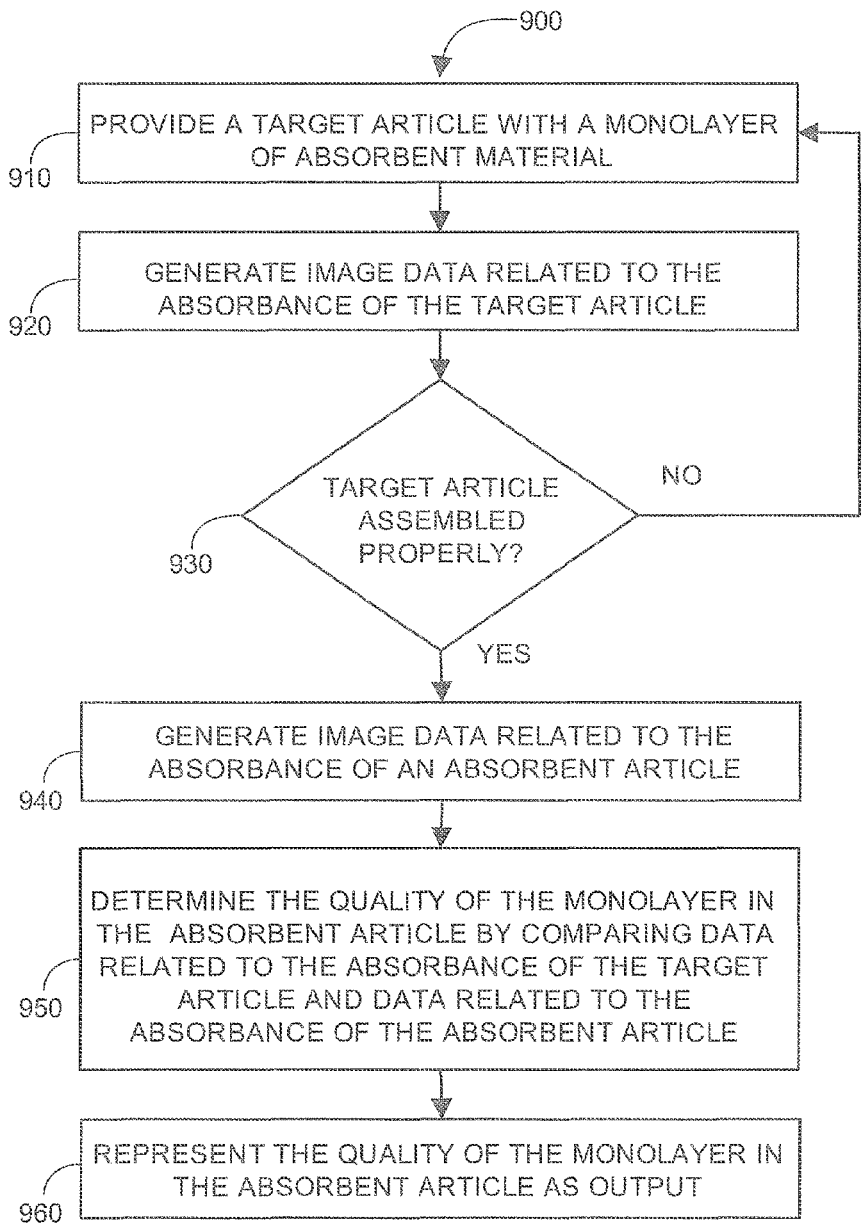
FIG. 9 is a flow diagram illustrating an example method for evaluating the AGM monolayer of an absorbent article.

FIG. 9 is a flow diagram illustrating an example method 900 for evaluating the AGM monolayer of an absorbent article using an AGM distribution evaluation system, such as the AGM distribution evaluation system 200 illustrated in FIG. 2. For ease of explanation, FIG. 9 will be described with reference to FIGS. 1-8. It will be understood, however, that the example method 900 for evaluating the monolayer of an absorbent article may be utilized with systems, devices and absorbent articles other than those illustrated in FIGS. 1-8.

In some embodiments, in order to characterize the monolayer, a target article that includes a monolayer of AGM granules may be provided to simulate an absorbent article with an AGM monolayer (block 910). Various attributes of the target article may then be determined, and the monolayer may be characterized based on these variables.

Figure 10:
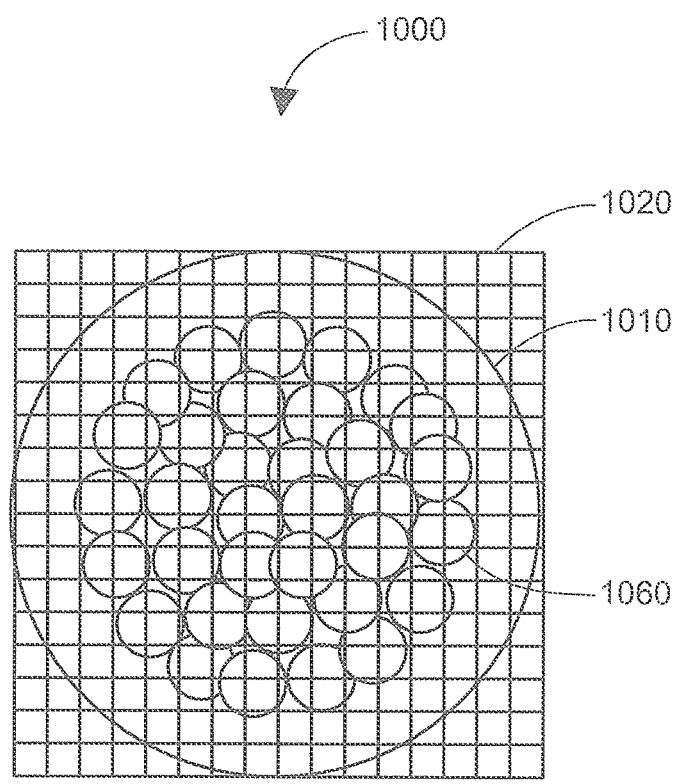
FIG. 10 illustrates an example target article that may be used to evaluate an AGM monolayer.

FIG. 10 illustrates an example target article 1000 that may be used to characterize the monolayer. The target article 1000 includes an AGM monolayer 1010, e.g., a surface that is substantially covered by AGM granules 1060 The target article 1000 may also include one or more layers (e.g., two layers) of nonwoven fabric 1020, or other material that may simulate the topsheet and the backsheet of an absorbent article.

As explained below, the monolayer of the target article may be characterized using infrared radiation of a particular wavelength range of interest (e.g., 3-3.2 µm), within which the infrared radiation is more likely to be absorbed by the absorbent material than by other materials within the target article. Therefore, it may be desired that the target article 900 not include any materials (other than the AGM granules 960) that substantially block infrared radiation within that wavelength range. Because sapphire does not substantially block infrared radiation in that wavelength range, a sapphire slide covered with AGM granules 960 and wrapped in nonwoven fabric 920 is one example of a suitable target article 900. However, it will be appreciated by one of ordinary skill in the art that other target articles may be used.

Referring again to FIG. 9, an AGM distribution imaging system, such as the AGM distribution imaging systems 305a-b illustrated in FIGS. 3A and 3B, may be used to generate image data indicative of the absorbance of the target article within the wavelength range of interest (block 920). As explained in reference to FIGS. 3A and 3B, a radiation source (such as radiation source 375) may transmit infrared radiation through different regions the target article, and a detector (such as the detector 380) may detect how much of that radiation was transmitted through each region of the target article. In particular, the detector may detect the number of photons transmitted through each region.

In some embodiments, in order to verify that the target article was assembled properly (block 930), various statistical checks may be performed on the generated data indicative of the absorbance of different regions of the target article. For example, it may be verified that the maximum detected number of photons (corresponding to a region with minimum absorbance) is within three standard deviations of the average detected number of photons across all regions. If so, the target article was assembled properly ("YES" branch of block 930). Otherwise ("NO" branch of block 930), a new target article may be provided (block 910).

If the target article was assembled properly ("YES" branch of block 930), the generated data regarding the absorbance of the target article may be used to evaluate the distribution of AGM in absorbent articles. For example, when imaging absorbent articles, the maximum detected number of photons transmitted through a region of a target article may be used as a threshold. A value below this threshold may indicate that an AGM granule is present, and a value above this threshold may indicate that an AGM granule is not present. The maximum detected number of photons transmitted through a region of a target article may also be used as the center of the "gray-area" range and/or of the color palette for an AGM distribution image, as described in reference to FIGS. 3A-3B.

Still further, if the target article was assembled properly ("YES" branch of block 930), the generated data regarding the absorbance of the target article may be used to evaluate the quality of the absorbent article. For example, the AGM distribution imaging system may be used to generate data indicative of an absorbance of infrared radiation within the wavelength range of interest incident on the absorbent article (block 940), and that data may be compared with the data related to the absorbance of the target article. In particular, the detector may detect the number of photons transmitted through each region of the absorbent article. If the detector detects that a certain region of the absorbent article transmitted more photons than the maximum detected number of photons transmitted through the target article, this may be an indication that the there is a "hole" in the AGM monolayer of the absorbent article, that an AGM monolayer is not present in the absorbent article, or that the AGM monolayer is of relatively poor quality, etc. If on the other hand, there are no regions in the absorbent article that transmitted more photons than the maximum detected number of photons transmitted through the target article, this may indicate that the absorbent article has an acceptable AGM monolayer. Therefore, generally, the quality of the AGM monolayer in the absorbent article may be determined by comparing the disparity between data related to the absorbance of the assembled target article and data related to the absorbance of the absorbent article (block 950).

The quality of the AGM monolayer in the absorbent article may be represented as output (960). This may be done in a variety of ways. For example, quality of the AGM monolayer may be quantified and presented as a value, e.g., via a user interface. Alternatively, various types of visual indicia indicative of the quality of the AGM monolayer may be presented to the user. It will be understood that may other techniques of representing the quality of the AGM monolayer in the absorbent article as output may be used.

Several example techniques for imaging and evaluating the distribution of an absorbent material in an absorbent article have been described above in terms of particular embodiments. However, other embodiments are possible. For example, various pre-processing steps, such as smoothing, binarization, thinning, and minutiae detection may be included in various embodiments to enhance the effectiveness of the techniques described above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this disclosure.

What is claimed is:

1. A system for imaging a distribution of an absorbent material within an absorbent article, the system comprising:
a radiation source configured to generate infrared radiation incident on an absorbent article comprising an absorbent material, the absorbent material having a spatial distribution within the absorbent article, wherein the infrared radiation within a particular wavelength range is more likely to be absorbed by the absorbent material than by other materials within the absorbent article, wherein the particular wavelength range is from 3 µm to 3.2 µm; and
a detector positioned such that the absorbent article is situated between the radiation source and the detector, the detector configured to:
detect a quantity of the infrared radiation within the particular wavelength range generated by the radiation source that was transmitted through a plurality of regions of the absorbent article; and
generate data indicative of the spatial distribution of the absorbent material based on the detected quantity of the infrared radiation corresponding to the plurality of regions of the absorbent article.

2. The system of claim 1, wherein the absorbent material is absorbent gelling material.

3. The system of claim 1, wherein the detector comprises a mid wave infrared camera capable of detecting infrared radiation in the particular wavelength range.

4. The system of claim 3, further comprising a filter situated between the radiation source and the detector, wherein the filter substantially blocks infrared radiation outside of the particular wavelength range.

5. The system of claim 1, wherein the detector is further configured to generate an absorbent material distribution image data representing the spatial distribution of the absorbent material within the absorbent article based on the data indicative of the spatial distribution of the absorbent material within the absorbent article.

6. The system of claim 5, wherein the absorbent material distribution image represents the spatial distribution of the absorbent material via visual indicia distinguishing one of a presence of an absorbent granule and a higher concentration of absorbent granules from a corresponding one of an absence of an absorbent granule and a lower concentration of absorbent granules.

7. The system of claim 6, wherein the absorbent material distribution image represents the spatial distribution of the absorbent material via visual indicia comprising one of a color, a monochromatic layer, a pixel intensity and a concentration of particular characters.

8. The system of claim 6, wherein the absorbent material distribution image is a grayscale image, wherein darker grayscale levels represent a higher concentration of absorbent granules and lighter grayscale levels represent a lower concentration of absorbent granules.

9. The system of claim 1, wherein the radiation source comprises a plurality of light sources configured to transmit the infrared radiation, wherein at least one of the plurality of light sources is a tungsten-halogen bulb.

10. The system of claim 9, wherein the radiation source further comprises a diffuser configured to diffuse the infrared radiation transmitted by the plurality of light sources to produce a substantially uniform radiation pattern across the absorbent article.

11. The system of claim 1, wherein the absorbent article is an assembled product from a group comprising a diaper, a sanitary napkin, a pantiliner, an incontinent pad, a breast pad, and a perspiration pad.

12. A method for evaluating a distribution of an absorbent material within an absorbent article, the method comprising:
using infrared imaging to generate image data with a radiation source configured to generate infrared radiation incident on the absorbent article, wherein the infrared radiation within a particular wavelength range is more likely to be absorbed by the absorbent material than by other materials within the absorbent article, wherein the particular wavelength range is from 3 µm to 3.2 µm, wherein the image data represents a spatial distribution of an absorbent material within an absorbent core of an absorbent article;
transforming the image data into one or more attribute values related to one or more attributes of the spatial distribution of the absorbent material; and
representing the one or more attribute values as output.

13. The method of claim 12, further comprising determining a quality of the absorbent article based on the one or more attribute values.

14. The method of claim 12, wherein the one or more attributes of the spatial distribution of the absorbent material comprises a shape of the spatial distribution formed by the absorbent material or a pattern of the spatial distribution formed by the absorbent material.

15. The method of claim 12, wherein the one or more attributes of the spatial distribution of the absorbent material comprises a quantity of the absorbent material within the absorbent core or a density of the absorbent material within the absorbent core.

16. The method of claim 12, wherein the one or more attributes of the spatial distribution of the absorbent material comprises an evenness of the spatial distribution of the absorbent material or presence of density transitions in the absorbent material.

17. The method of claim 12, wherein the one or more attributes of the spatial distribution of the plurality of absorbent granules comprises presence of islands of absorbent material or presence of regions with no absorbent material.

18. The method of claim 12, wherein determining the quality of the absorbent article comprises determining a disparity between the determined one or more attributes of the spatial distribution of the absorbent material and a corresponding one or more desired attributes of the spatial distribution of the absorbent material.

* * * * *